United States Patent [19]
Fisher

[11] Patent Number: 6,066,122
[45] Date of Patent: May 23, 2000

[54] NEEDLE APPARATUS AND METHOD FOR MARKING LESIONS

[76] Inventor: John Fisher, 603 Ponce de Leon, Bellair, Fla. 33756

[21] Appl. No.: 09/328,531

[22] Filed: Jun. 9, 1999

[51] Int. Cl.[7] .................................................. A61M 25/00
[52] U.S. Cl. .......................... 604/500; 604/508; 604/528; 604/164
[58] Field of Search .................................... 604/500, 502, 604/506, 507, 508, 523, 525, 528, 264, 272, 164

[56] References Cited

U.S. PATENT DOCUMENTS

| 4,349,023 | 9/1982 | Gross | 604/164 |
| 5,011,473 | 4/1991 | Gatturna | 604/528 |
| 5,487,729 | 1/1996 | Avellanet et al. | 604/528 X |
| 5,522,818 | 6/1996 | Keith et al. | 604/525 |

Primary Examiner—John D. Yasko
Attorney, Agent, or Firm—Ronald E. Smith; Smith & Hopen, P.A.

[57] ABSTRACT

An elongate side port of small circumferential extent is formed in a hollow bore needle of the type used for marking the location of a lesion or a tumor in a breast or soft tissue. A wire carrier housing an elongate flexible marking wire is slideably received within the hollow bore. The needle, wire carrier and wire are inserted into a breast or soft tissue so that the side port is facing a lesion. After position adjustments have been made, if needed, the wire is advanced so that its distal end is deflected through the side port by a radius formed in the distal end of the wire carrier. When extended, it marks the location of the lesion and anchors the wire against migration. If the position of the needle is then understood to be unsatisfactory, the marking wire is withdrawn through the side port and back into the wire carrier and the needle is withdrawn and then re-positioned. When the position is deemed satisfactory, the needle and wire carrier are withdrawn and the physician follows the marking wire to its distal end to remove the lesion.

4 Claims, 5 Drawing Sheets

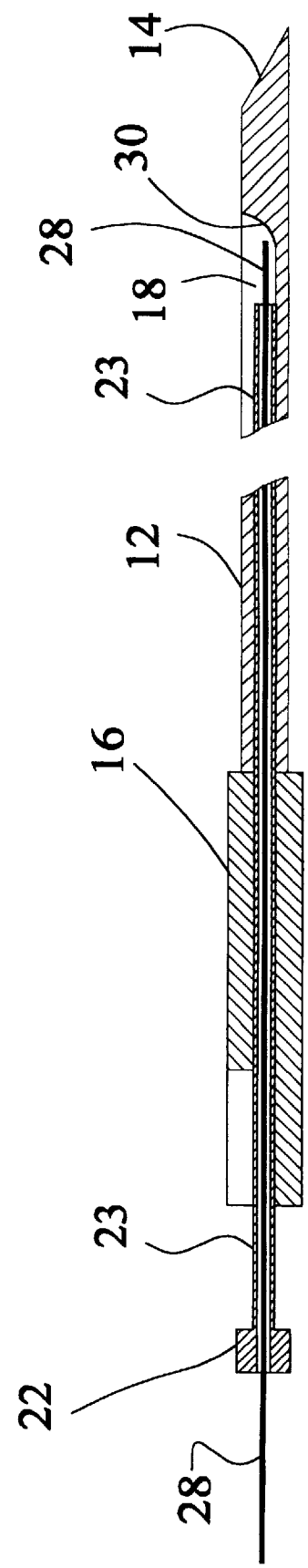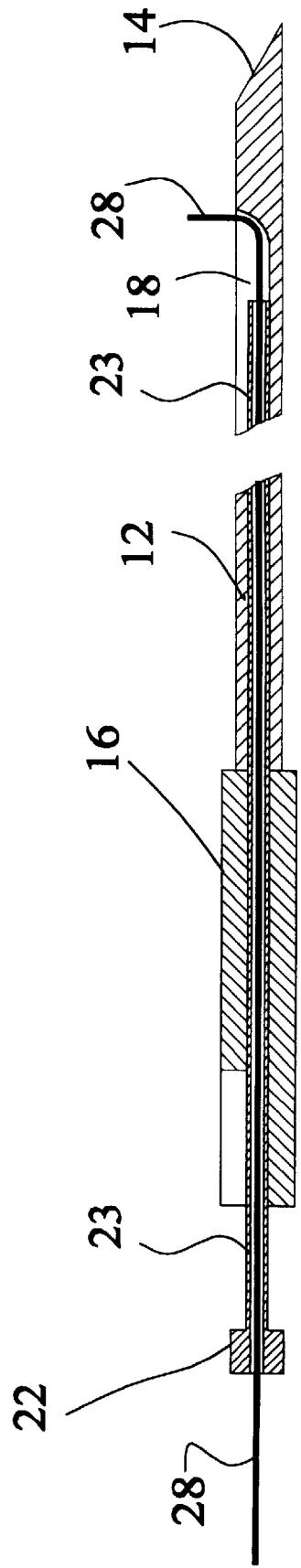

NEEDLE APPARATUS AND METHOD FOR MARKING LESIONS

BACKGROUND OF THE INVENTION

1. Field of the Invention

This invention relates, generally, to surgical tools and methods for their use. More particularly, it relates to a needle apparatus and method for marking the location of a lesion or a tumor in a breast or soft tissue.

2. Description of the Prior Art

Mammography enables the detection of very small lesions or tumors in a breast, even if the individual is experiencing no symptoms. However, if the lesion or tumor is non-palpable, it can be difficult for the surgeon to locate it and remove it through surgery.

A lesion may be non-palpable because it is very small. It may even be relatively large, but still non-palpable because it resides in a large breast or in a smaller breast but deep within the tissue mass.

In one prior art procedure, developed by Kopans, a hypodermic needle is placed into the breast so that the tip of the needle is near the lesion.

After the needle tip is positioned near the lesion, a stainless steel marking wire having a thin hooked distal end is introduced into the proximal end of the hollow bore of the needle and pushed toward the lesion until the thin hooked distal end of the marking wire protrudes from the distal end of the needle. The hook engages the breast tissue in the vicinity of the lesion and holds the marking wire in place, at least to some extent. Additional mammograms are then taken to verify the respective positions of the needle, the marking wire, and the hook. If the position of the apparatus is satisfactory, the needle is withdrawn from the breast, leaving the stainless steel marking wire unmoved because it is not connected to the needle. The surgeon then follows the marking wire to the lesion and removes the tissue in the vicinity of the hook.

The breast, however, must be compressed during the taking of a mammogram. The compression often causes the needle to migrate during mammagraphic filming; this causes uncertainty about the location of the hook.

Moreover, if the position of the hook is determined to be unsatisfactory, i.e., too far from the lesion, the hook cannot be extracted in any satisfactory manner. For example, forceful retraction of the marking wire can damage breast tissue; the hook might even break off and be lost in the tissue mass. Leaving a hook in the patient is unacceptable. Thus, another marking wire must be used in an additional attempt to position it closer to the lesion. It is not uncommon for several marking wires to protrude from a breast because multiple attempts to properly position a wire have been unsuccessful. This creates anxiety in the patient.

The most commonly used marking wire has an enlarged diameter near its distal end. The enlarged part purportedly makes the distal end palpable, but in practice it does not perform that intended function.

What is needed, then, is an improved method for marking the position of a breast or soft tissue lesion or tumor. The new method should facilitate additional attempts to better position the needle if the initial needle insertion proves to be unsatisfactory. There should be no tissue damage caused by withdrawing a wire hook and there should be no broken hooks left within a breast or other soft tissue.

However, it was not obvious to those of ordinary skill in this art how the needed method could be provided, in view of the art considered as a whole at the time the present invention was made.

SUMMARY OF THE INVENTION

The long-standing but heretofore unfulfilled need for an innovation that overcomes the limitations of the prior art is now met by a new, useful, and nonobvious invention. The present invention includes a method for marking the location of a lesion or tumor in a breast or other soft tissue. It includes the steps of providing an elongate, thin marking wire having flexibility and resilience and inserting that wire into tissue by means of a wire carrier that enables the wire to be withdrawn from the tissue without harming the tissue and without wire breakage if a wire needs to be withdrawn and repositioned.

The marking wire may also be prestressed at a preselected location near its distal end so that it is self-biased to bend at a preselected angle with respect to its longitudinal axis.

The marking wire is introduced into an interior bore of an elongate wire carrier having a relatively rigid construction so that the marking wire is held in a substantially straight configuration along its extent. The wire carrier and marking wire therein are introduced into an interior bore of a hollow needle having a pointed distal end and an elongate side port formed therein. The hollow needle having the wire carrier and marking wire therein is inserted into a breast or soft tissue so that the hollow needle is adjacent to a lesion. The depth of insertion is adjusted and the hollow needle is rotated until the side port is facing the lesion.

The wire carrier has a closed distal end and a radius formed just proximal to the distal end so that when the marking wire is advanced in a proximal-to-distal direction, the distal end of the marking wire is deflected radially outwardly by the radius through the side port.

The hollow needle and the wire carrier are then withdrawn, leaving the marking wire in position so that its distal end serves as a marker for the location of the lesion.

Significantly, if the location of the marking wire is determined to be in need of adjustment, the marking wire is simply retracted into the wire carrier. When retracted, the wire re-traces its initial path of travel as it extended through the side port formed in the hollow needle. This ensures that the wire will not damage tissue as it is withdrawn and further ensures that the distal end of the wire will not break off. The wire carrier can then be repositioned as needed.

The side port formed in the hollow needle has a predetermined longitudinal and circumferential extent. The circumferential extent of the side port is greater than a diameter of the marking wire so that the distal end of the marking wire may extend through the side port. The distal end of the marking wire serves as a location marker for a lesion or tumor.

The apparatus further includes a plurality of longitudinally, equidistantly spaced apart indicia on an exterior surface of the wire carrier so that a physician may determine its depth of insertion into a breast or soft tissue by observing the indicia.

It is a primary object of this invention to advance the art of marking the location of non-palpable lesions or tumors in a breast or soft tissue.

A more specific object is to provide a method for marking lesions or tumors that enables a physician to make multiple attempts, if needed, to place a marker needle near a lesion without inflicting trauma upon breast or soft tissue.

Another very important object is to enable such multiple attempts without risk of breaking a marking wire and thus without risk of leaving a broken wire in a breast or soft tissue.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 3A is a longitudinal sectional view of the novel wire carrier when the marking wire is fully received therewith;

FIG. 3B is a longitudinal sectional view of the novel wire carrier when the marking wire is extended therefrom;

DETAILED DESCRIPTION OF THE PREFERRED EMBODIMENT

Figure 1:
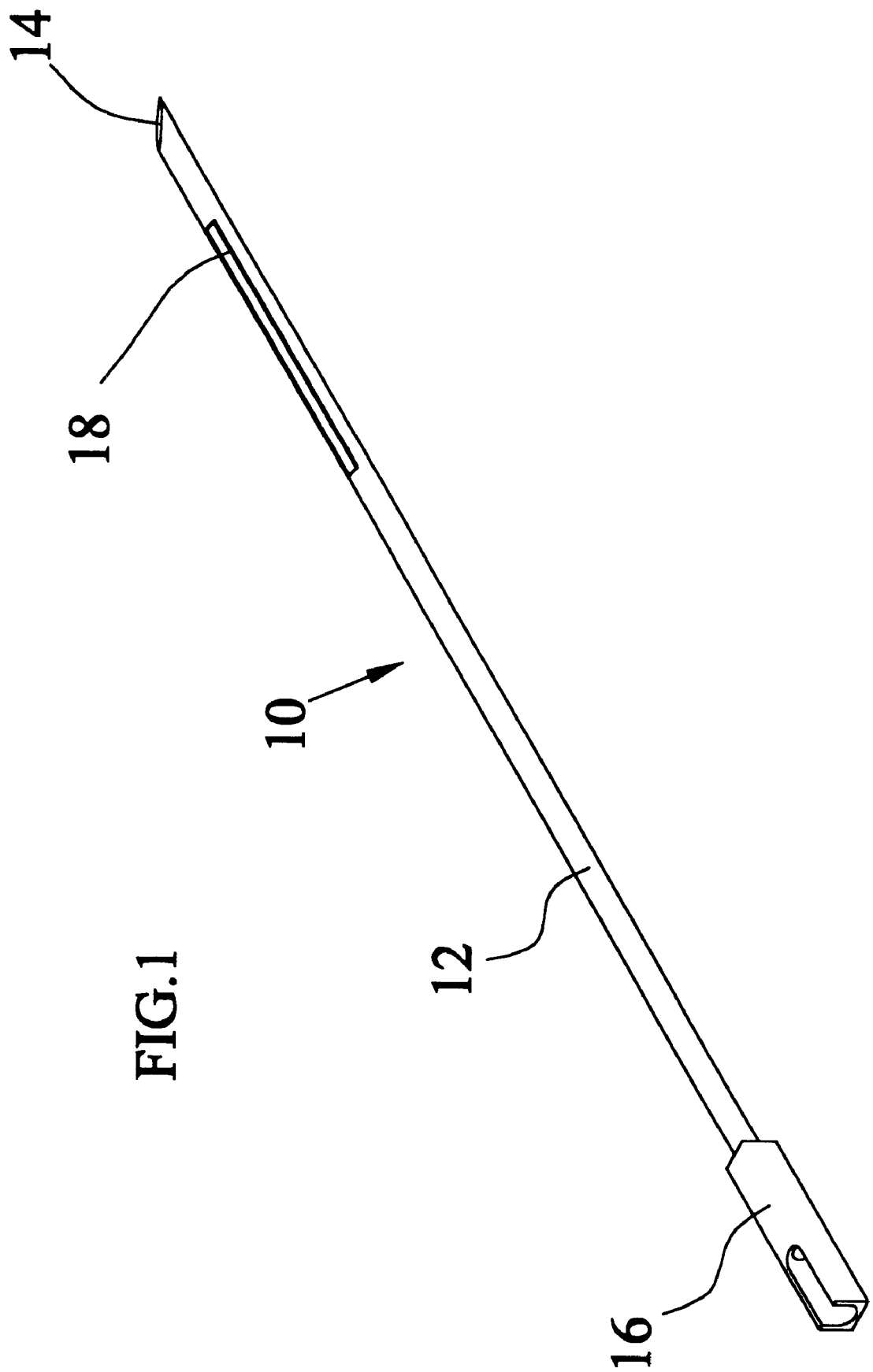
FIG. 1 is a perspective view depicting the hollow needle having a side port.

Referring now to FIG. 1, it will there be seen that a novel hollow needle that forms a part of the apparatus of this invention is denoted as a whole by the reference numeral 10.

Needle 10 includes hollow main body 12 having a sharpened tip 14 at its leading or distal end and a hub 16 at its trailing or proximal end 16 for slideably receiving a wire carrier that is not illustrated in FIG. 1.

An elongate port, hereinafter referred to as side port 18, is formed in needle 12. It has an elongate, narrow, circumferentially-extending extent.

Figure 2:
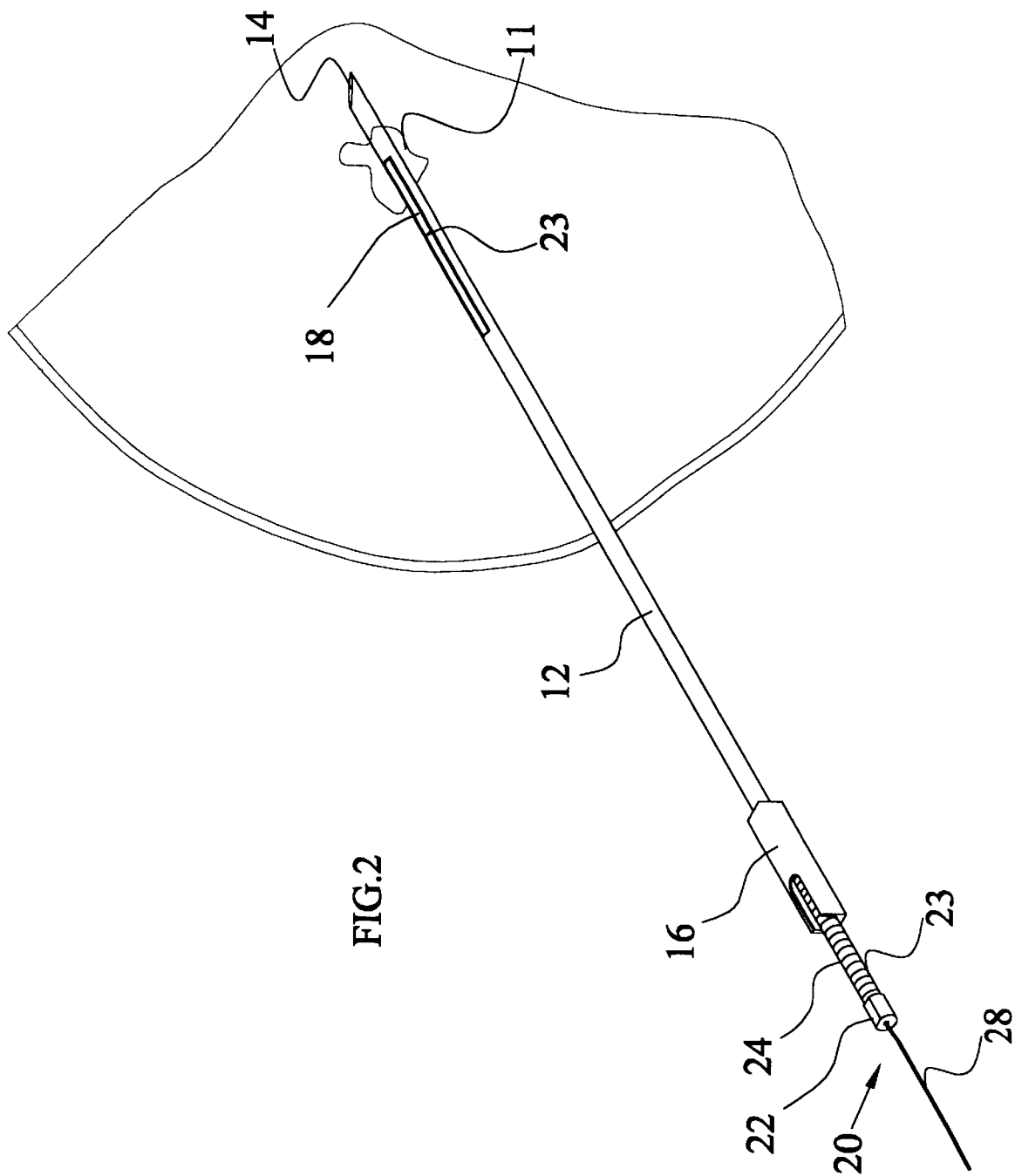
FIG. 2 is a perspective view depicting the first step of the novel method.

As indicated in FIG. 2, apparatus 10 further includes a wire carrier 20 having proximal end 22 and a main body 23. Note that a flat key is formed in proximal end 22 and is facing upwardly in FIG. 2.

Wire carrier 20 has an external diameter slightly less than the internal diameter of the hollow bore of needle main body 12 and said wire carrier 20 is slideably received within said internal bore.

Markings 24 are provided at one centimeter intervals along the external surface of wire carrier main body 23 so that its depth of axial insertion may be observed and adjusted as needed.

A flexible and resilient marking wire 28 is slideably positioned within said wire carrier 20. In a first embodiment, the wire is straight but its flexibility enables it to be deflected in a manner set forth hereinafter.

In an alternative embodiment, a preselected region of marking wire 28 is pre-stressed to bend near the distal end thereof to form a hook in its leading end. The distal end thereof therefore extends radially outwardly under a self-bias, forming a hook shape, with respect to the longitudinal axis of the wire when the wire is not constrained by wire carrier 20.

In FIG. 2, if the hooked wire of the alternative embodiment is used, the upwardly facing flat formed in proximal end 22 indicates to the physician that the bent distal end of marking wire 28 is rotated one hundred eighty degrees away from side port 18. This ensures that said bent distal end will not inadvertently extend through said side port.

Wire carrier 20 is positioned within the hollow bore of needle main body 12 before the surgical procedure begins.

As depicted in FIG. 2, needle main body 12, having wire carrier 20 and wire 28 therewithin, is first inserted into a breast in impaling relation to a lesion or tumor 11.

If a mammographic view shows that needle main body 12 is not well positioned, it is simply withdrawn, together with wire carrier 20 and wire 28, and another attempt is made to position the needle near the lesion.

If the mammogram indicates that the needle is well positioned, but that wire carrier 28 is inserted too far or too little, the physician advances or retracts said wire carrier, making reference to graduations 24, until the amount of insertion is optimal. During this advancing and retracting of wire carrier 20, wire 28 is fully received within said wire carrier 20. If the alternative marking wire is used, its pre-stressed distal end is constrained against bending by said wire carrier.

After needle 10 and wire carrier 20 are satisfactorily positioned, wire carrier 20 and hence marking wire 28 are rotated about their common longitudinal axis of symmetry until radius 30 formed in wire carrier 20 (see FIGS. 3A and 3B) aligns with side port 18. Marking wire 28 is then advanced in a proximal-to-distal direction, and radius 30 deflects the leading or distal end of marking wire 28 through side port 18 and into the soft tissue near the lesion or tumor 11.

Figure 4:
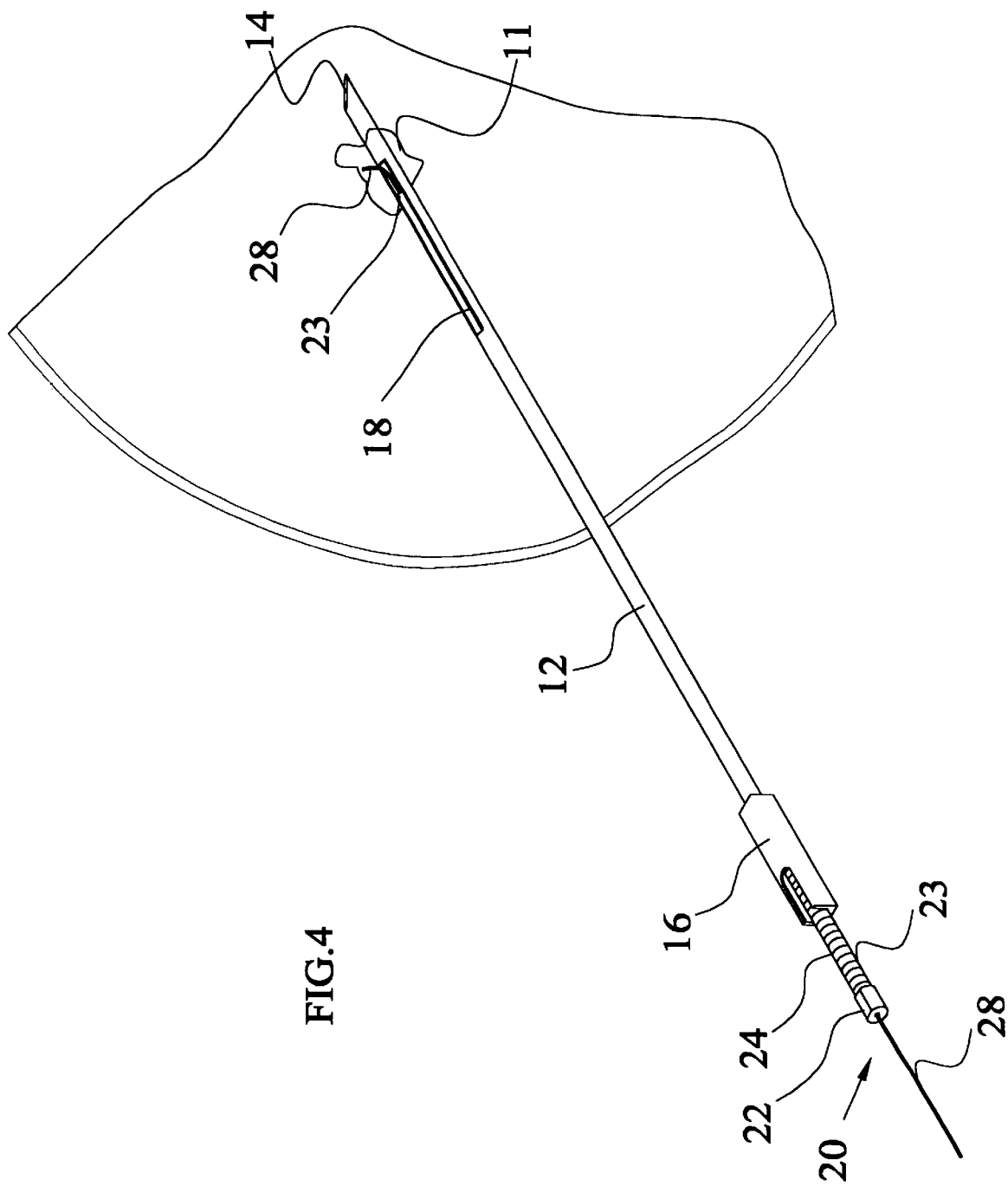
FIG. 4 is a perspective view depicting the novel apparatus when the marking wire is extended through the side port of the hollow needle.

FIG. 4 depicts the distal end of wire 28 extending through side port 18 into lesion 11.

Figure 5:
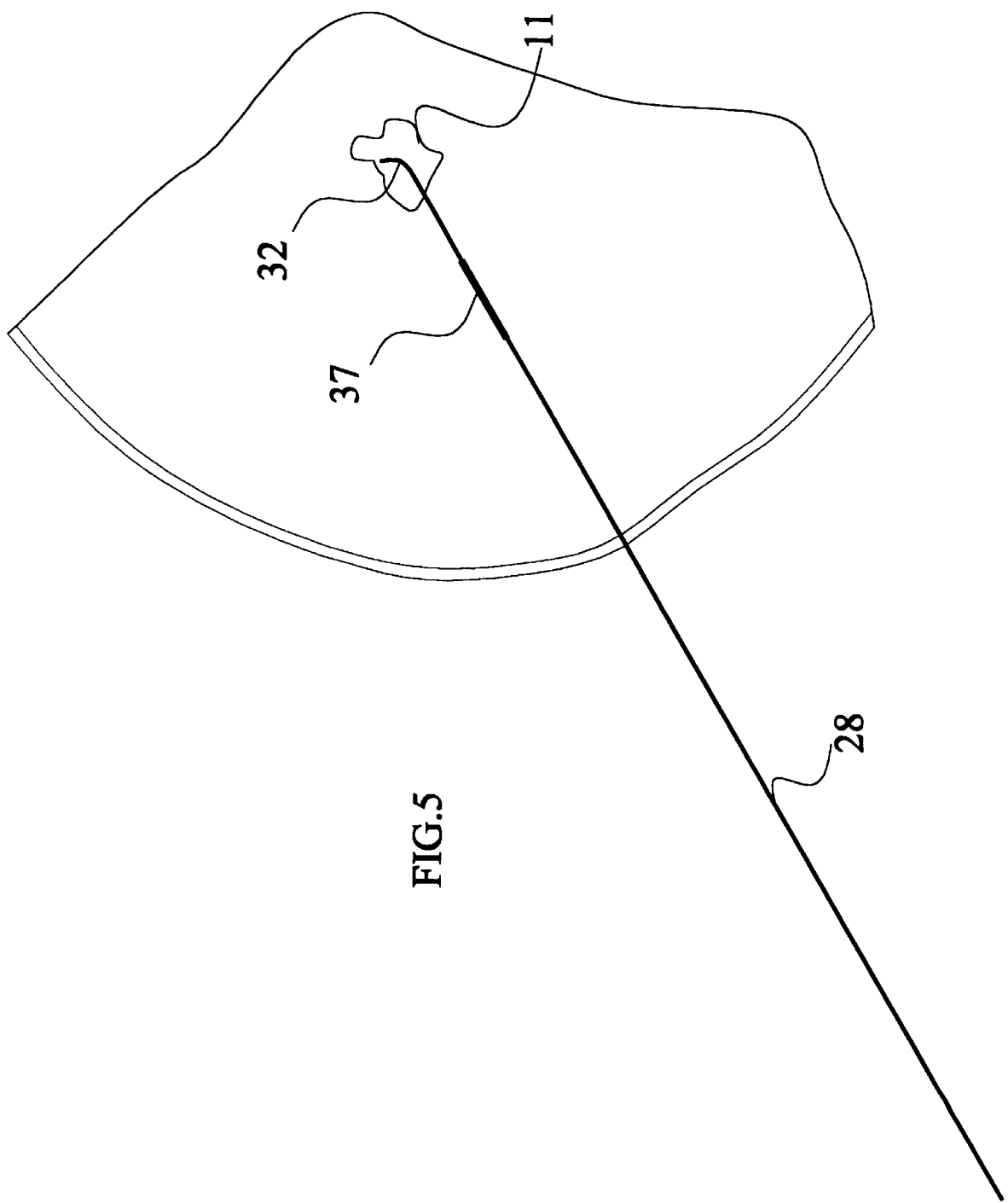
FIG. 5 is a perspective view depicting the marking needle in position after the hollow needle and wire carrier have been withdrawn.

Needle 10 and wire carrier 20 are then withdrawn, leaving marking wire 28 in the position indicated in FIG. 5. The surgeon then follows the wire to distal end 32 thereof and removes the surrounding tissue as in prior art methods.

If the position of distal end 32 indicates that the position of needle 10 is unsatisfactory, marking wire 28 is retracted back into wire carrier 20 and hence back into needle 10 so that another attempt can be made to reposition the needle closer to the lesion. Such retraction of distal end 32 does not damage breast tissue. Distal end 32 can be extended and retracted through side port 18 many times to enable the physician to properly position marking wire 28.

Marking wire 28 and its distal end 32 may be provided in differing shapes. Thus, marking wires and distal ends of differing shapes could identify different lesions. Differing wire shapes and distal ends of differing shapes could also be employed to identify a single lesion with more than one marking wire.

A prior art marking wire having purportedly palpable enlargement 37 may also be used with this novel assembly.

It will thus be seen that the objects set forth above, and those made apparent from the foregoing description, are efficiently attained. Since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A method for marking the location of a lesion or tumor in a breast or soft tissue, comprising the steps of:

providing a thin, elongate marking wire having flexibility and resilience;

providing an elongate wire carrier and introducing said marking wire into an interior bore of said elongate wire carrier;

forming a radius in said elongate wire carrier near a distal end thereof so that advancing said marking wire in a proximal-to-distal direction causes a distal end of said marking wire to be deflected radially outwardly by said radius;

providing an elongate hollow needle having a pointed distal end and having an elongate side port formed therein;

introducing said wire carrier and marking wire therein into an interior bore of said elongate hollow needle;

inserting said hollow needle having said wire carrier and marking wire therein into soft tissue so that the hollow needle impales a lesion;

adjusting the depth of said insertion and rotating said hollow needle until said side port is in a predetermined orientation;

rotating the wire carrier until the radius formed therein is in rotational alignment with said side port;

advancing said marking wire in a proximal-to-distal direction so that said distal end of said marking wire is deflected by said radius so that said distal end extends through said side port and is positioned in said lesion; and withdrawing the hollow needle and the wire carrier, leaving the marking wire in position so that its distal end serves as a marker for the location of said lesion.

2. The method of claim 1, further comprising the step of initially positioning said wire carrier in a preselected position of rotational adjustment relative to said elongate hollow needle so that said marking wire cannot extend through said side port.

3. An apparatus for marking the location of a breast lesion or tumor, comprising:

an elongate marking wire that is flexible and resilient;

an elongate wire carrier having an interior bore sized to house said marking wire;

a deflector means having a radius formed therein adjacent a distal end of said wire carrier;

an elongate hollow needle having a side port formed therein of predetermined longitudinal and circumferential extent;

said circumferential extent of said side port being greater than a diameter of said marking wire so that said distal end of said marking wire may extend through said side port when said distal end is deflected through said side port by said deflector means;

said distal end serving as a location marker for a lesion or tumor when said distal end extends through said side port.

4. The apparatus of claim 3, further comprising a plurality of longitudinally, equidistantly spaced apart indicia on an exterior surface of said wire carrier so that a physician may determine its depth of insertion into said hollow needle by observing said indicia.

* * * * *